(12) United States Patent
Bruchmann et al.

(10) Patent No.: US 7,786,240 B2
(45) Date of Patent: Aug. 31, 2010

(54) PRODUCTION AND USE OF HIGHLY FUNCTIONAL, HIGHLY BRANCHED OR HYPERBRANCHED POLYLYSINES

(75) Inventors: Bernd Bruchmann, Freinsheim (DE); Harm-Anton Klok, St. Sulpice (CH); Markus Thomas Scholl, Lausanne (CH)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/093,773

(22) PCT Filed: Nov. 15, 2006

(86) PCT No.: PCT/EP2006/068479

§ 371 (c)(1),
(2), (4) Date: May 15, 2008

(87) PCT Pub. No.: WO2007/060119

PCT Pub. Date: May 31, 2007

(65) Prior Publication Data

US 2009/0048416 A1    Feb. 19, 2009

(30) Foreign Application Priority Data

Nov. 25, 2005  (DE) .................... 10 2005 056 592

(51) Int. Cl.
*C08G 69/00* (2006.01)
*C08G 69/08* (2006.01)
(52) U.S. Cl. .................... 528/15; 528/310; 528/318; 528/328
(58) Field of Classification Search .................... 528/15
See application file for complete search history.

(56) References Cited

U.S. PATENT DOCUMENTS 3,907,755 A    9/1975   Margraff et al.
6,777,527 B1 *  8/2004   Mohr et al. .................. 528/328

FOREIGN PATENT DOCUMENTS

WO    WO 00/71600 A1   11/2000
WO    WO 03/064452 A2   8/2003

OTHER PUBLICATIONS

Vlasov G.P., et al.,"Hyperbranched Poly(L-lysine) Containing Additional Amino Acids or Their Oligomers Between Branching Points: Synthesis and Structure[1]", Polymer Sciences Ser. A, vol. 47, No. 5, May 2005, pp. 422-429, XP008074529.
Menz T.L., et al., "Synthesis and Characterization of Hyperbranched Polylysine" Polymer Prepints, 2003, vol. 44, No. 2, pp. 842-843, XP008074519.
Klok H.A., et al.,"Dendritic—Graft Polypeptides", Macromolecules, American Chemical Society, Washington, DC, US, Nov. 2002, vol. 35, pp. 8718-8723, XP002250744.
Rodriguez-Hernandez, J., et al., "Rapid Synthesis of Highly Branched Polypeptides" American Chemical Society, Abstracts of paper at the national Meeting, American Chemical Society, Washington, DC, US, vol. 224, 2002 p. 428, XP009014378.
Rogriguez-Hernandez J., et al., "Highly Branched Poly(L-lysine)", Biomacromolecules, American Chemical Society, Washington , DC, US, vol. 4, No. 2, Mar. 2003, pp. 249-258, XP002250742.
Flory P.J., "Molecular Size Distribution in Three Dimensional Polymers. VI. Branched Polymers Containing A-R-$B_{f-1}$ Type Units", Journal American Chemical Society, Jun. 5, 1952, vol. 74, pp. 2718-2723.
Hoelter, et al., "Degree of branching in hyperbranched polymers", Acta Polymer, 1997, vol. 48, pp. 30-35.
Birchall A. C., et al.,"Synthesis of highly branched block copolymers of enantiomerically pure amino acids", Chem. Commun., 1998, pp. 1335-1336.
Hennon G., et al., "The synthesis of amino acid polymers by thermal condensation at 105° C without a catalyst", Biochimie, 1975, vol. 57, No. 11-12, pp. 1395-1396.
Harada K., "Thermal Homopolymerization of Lysine and Copolymerization with Neutral and Acidic Amino Acids", Bull. Chem. Soc., Japan , Sep. 1959, vol. 32, No. 9, pp. 1007-1008.
Heinrich, M.R., et al. "The Effect of Time of Heating on the Thermal Polymerization of L-Lysine", Archives of Biochemistry and Biophysics, 1969, vol. 130, pp. 441-448.
Fox S. W., et al., "Linkages in Thermal Copolymers of Lysine", BioSystems, Vo. 8, 1976, pp. 40-44.
Sunder A., "Controlling the Growth of Polymer Trees: Concepts and Perspectives for Hyperbranched Polymers", Chem. Eur. Journal, 2000, vol. 6, No. 14, pp. 2499-2506.

* cited by examiner

*Primary Examiner*—Ling-Siu Choi
*Assistant Examiner*—Chun-Cheng Wang
(74) *Attorney, Agent, or Firm*—Oblon, Spivak, McClelland, Maier & Neustadt, L.L.P.

(57) ABSTRACT

The present invention relates to new high-functionality, highly branched or hyperbranched polylysines, to processes for preparing them, and to their use.

Figure 1:
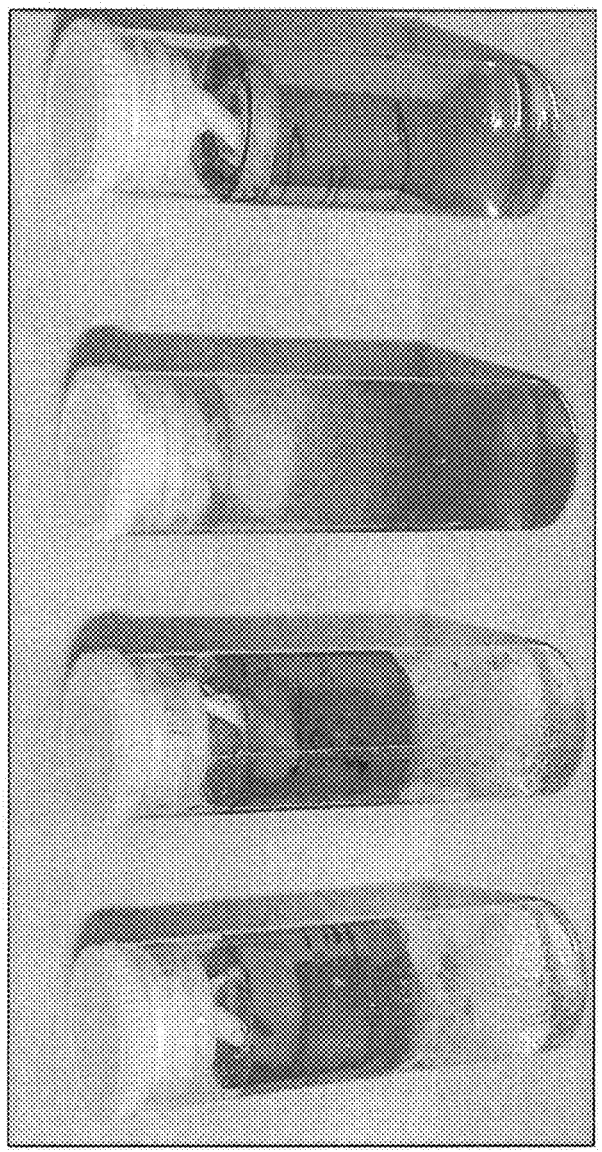

12 Claims, 1 Drawing Sheet
(1 of 1 Drawing Sheet(s) Filed in Color)

PRODUCTION AND USE OF HIGHLY FUNCTIONAL, HIGHLY BRANCHED OR HYPERBRANCHED POLYLYSINES

The present invention relates to new high-functionality, highly branched or hyperbranched polylysines, to processes for preparing them, and to their use.

Both in research and in industry there is increasing interest in dendrimeric and hyperbranched polypeptides. Potential biomedical applications exist for example in the development of new multiple antigen peptides (MAPs), as a carrier platform of contrast agents for magnetic resonance imaging or as gene transporters.

Dendritic polymers with a perfectly symmetrical structure, referred to as dendrimers, can be prepared, starting from a central molecule, by controlled, stepwise linkage of two or more difunctional or polyfunctional monomers in each case with each monomer already attached. With each linkage step in this procedure there is an increase in the number of monomer end groups (and hence of linkages), and polymers are obtained which have treelike structures, ideally spherical, whose branches each comprise exactly the same number of monomer units. This perfect structure confers advantageous properties on the polymer, with observations including, for example, a surprisingly low viscosity and a high reactivity owing to the large number of functional groups on the surface of the sphere. Preparation is complicated, however, by the fact that each linkage step requires the introduction and removal of protective groups, and purifying operations, and for these reasons dendrimers are typically prepared only on the laboratory scale.

Dendritic polymers with a less perfect structure, referred to as hyperbranched polymers, can be prepared in contrast by industrial processes. Besides perfect dendrimeric structures, hyperbranched polymers also contain linear polymer chains and unequal polymer branches, although this does not substantially impair the polymer properties as compared with those of the perfect dendrimers.

Hyperbranched polymers can be prepared by what is called the AB2 route. An AB2 molecule is a term used to refer to a trifunctional monomer containing one reactive group A and two reactive groups B. Where these groups A and B are reactive with one another, hyperbranched polymers can be produced by intermolecular reaction.

Regarding the definition of dendrimeric and hyperbranched polymers see also P. J. Flory, J. Am. Chem. Soc. 1952, 74, 2718 and H. Frey et al., Chemistry—A European Journal, 2000, 6, No. 14, 2499.

By "hyperbranched" is meant in the context of the present invention that the degree of branching (DB) is 10% to 99.9%, preferably 20% to 99%, more preferably 20%-95%.

By "dendrimeric" is meant in the context of the present invention that the degree of branching is 99.9%-100%.

The degree of branching is defined as follows:

$$DB[\%]=100*(T+Z)/(T+Z+L)$$

where T denotes the average number of terminal monomer units, Z the average number of branched monomer units, and L the average number of linear monomer units. With regard to the definition of the degree of branching see also H. Frey et al., Acta Polym. 1997, 48, 30.

By hyperbranched polypeptides are meant, in the context of this invention, non-crosslinked macromolecules synthesized from amino acids, which possess not only structural but also molecular nonuniformity. On the one hand they can be synthesized, starting from a central molecule, in analogy to dendrimers, but with a nonuniform chain length in the branches. On the other hand they can also be synthesized linearly, with functional side groups, or else, as a combination with the two extremes, can have linear and branched moieties.

For the synthesis of hyperbranched polylysines there are three processes known in principle:

Process 1 is based on the ring-opening addition polymerization of ε-protected L-lysine-N-carboxyanhydrides (NCAs) with a nucleophilic starter;

Process 2 uses derivatives of L-lysine*2HCl that are activated on the carboxyl group;

Process 3 involves the direct thermal addition polymerization of L-lysines.

Process 1, Hyperbranched L-Lysine Polymers Based on the Ring-Opening Addition Polymerization of ε-Protected L-Lysine-N-Carboxyanhydrides:

Hyperbranched poly(L-lysines) have been described by Klok et al. (WO 2003/064452 and *Macromolecules* 2002, 35, 8718-8723). Orthogonally $N^\epsilon$-protected butoxycarbonyl-L-lysine (Boc-lysine; =temporary protective group) and ε-benzyloxycarbonyl-L-lysine (Z-lysine; =permanent protective group) NCAs were subjected to ring-opening polymerization using an aliphatic amine (e.g., hexylamine) as starter. The temporary protective group was removed using trifluoroacetic acid (TFA), and the free amino groups were employed as further starters for a new polymerization. In the last step the Z protective groups were eliminated using hydrogen bromide/acetic acid (HBr/AcOH).

Additionally, hyperbranched poly(L-lysines) have been described by Rodriguez-Hernández et al. (*Biomacromolecules* 2003, 4, 249-258). A mixture of $N^\epsilon$-trifluoroacetyl-L-lysine-NCA (TFA-Lys-NCA) and Z-lysine-NCA were subjected to ring-opening polymerization with an aliphatic amine. In a separate coupling step $N^\alpha,N^\epsilon$-di(9-fluorenylmethoxycarbonyl)-L-lysine ($N^\alpha/N^\epsilon$-diFmoc Lys) was introduced as a branching point. Deprotection with piperidine in DMF gave two new amine groups, which allow ring-opening polymerization of TFA-Lys-NCA and Z-Lys-NCA. These reaction cycles were repeated a number of times. Structurally similar hyperbranched block copolymers have also been described by Birchall et al. (*Chem. Commun.* 1998, 1335-1336). α-Amino acid NCAs were subjected to ring-opening polymerization with an aliphatic amine. N,N'-Di(benzyloxycarbonyl)-L-lysine p-nitrophenyl ester was introduced as a branching point, and after deprotection of $H_2$/Pd/C had two free amine groups for the further ring opening of amino acid NCAs. These reaction cycles were repeated a number of times.

A disadvantage of all of these reaction regimes is that protective groups are required, which makes the reaction substantially more difficult.

Process 2, Hyperbranched L-Lysine Polymers Based on Derivatives of L-Lysine*2HCl which are Activated on the Carboxyl Group.

Hyperbranched polylysines were prepared in a one-pot synthesis with activation of the carboxyl group by means of N-hydroxysuccinimide (NHS). NHS-activated L-lysine*2HCl was stirred for 23 hours in dimethyl sulfoxide (DMSO) with the addition of catalytic amounts of dimethylaminopyridine (DMAP) and 3 equivalents of diisopropylethylamine (DIEA), and the polymer was precipitated from ethyl acetate. The polymer had a molecular weight of Mw=5100. Using the same reagents in a "pseudo stepwise"

polymerization, with repeated addition of monomer, molecular weights of Mw=8640 were attained. Additionally, the monomer was also polymerized onto tris(2-aminoethyl)-amines as a core molecule. In this regard see also T. L. Menz and T. Chapman, Polym. Prep. 2003, 44(2), 842-743.

A disadvantage of the reaction regime disclosed by Menz is that the carboxyl function has to be activated by a specialty reagent, so complicating the reaction regime.

Process 3, Thermal Addition Copolymerizations of Amino Acid Mixtures:

The thermal addition polymerization of free lysine is known and has been carried out under various reaction conditions.

Plaquet and coworkers (*Biochimie* 1975, 57 1395-1396) polymerized L-lysine in aqueous solution at 105° C. for a period of up to 10 weeks, or else by heating at 165° C. for 8 hours. The reaction was carried out without catalyst and the yields, at below 72.5% without exception, were very low.

Harada (Bull. Chem. Soc. Japan 1959, 32, 1007-1008) polymerized L-lysine at 180 to 230° C. for between 30 minutes and 2 hours under a nitrogen atmosphere. In a reaction below 180° C. only the formation of lactams is reported. Nothing is reported concerning molecular weight of a structure. The homopolymers obtained have a marked gel fraction. The homopolymerization of lysine hydrochloride was not achieved (p. 1008, bottom of left-hand column).

Rohlfing and coworkers (*Archives of Biochemistry and Biophysics* 1969, 130, 441-448) polymerized L-lysine (free base) under a nitrogen atmosphere at between 186 and 192° C. They attained molecular weights of up to 3600 Da and higher. Branched fractions as well were hypothesized here (see comparative experiment 11). The molecular weights >100 000 described by Rohlfing et al. were not found in the comparative experiment.

WO 00/71600 describes the condensation of L-lysine monohydrate in a pressure apparatus. The molecular weights of the homopolymers obtained are low. Condensation of the free lysine base leads to crosslinked condensation products and is carried out either without catalysis or by catalysis with mineral acids or salts thereof. Hydrochlorides must be converted pre-reaction into the free base, using one equivalent of base, before they can be reacted in accordance with WO 00/71600.

Fox et al. (*BioSystems* 1976, 8, 40-44) used not only L-lysine but also L-lysine*HCl as starting monomers for the thermal polymerization at 195° C. In this case, when using L-lysine at a reaction temperature of 170° C., the cyclic lactam was obtained. L-Lysine*HCl was brought to reaction only with the addition of orthophosphoric acid at 195° C. The molecular weights obtained here were low (see comparative experiment 12).

It was an object of the present invention to provide a simple process for preparing polylysines that does not require protective-group operations or activation of carboxyl groups and in which it is also possible to attain higher molecular weights than those known from the prior art.

The object has been achieved by means of a process for preparing noncrosslinked hyperbranched polylysines by reacting (A) a salt of lysine with at least one acid, (B) if appropriate, at least one amino acid other than lysine, (C) if appropriate, at least one dicarboxylic or polycarboxylic acid or copolymerizable derivatives thereof and (D) if appropriate, at least one diamine or polyamine or copolymerizable derivatives thereof, (E) if appropriate, in at least one solvent at a temperature from 120 to 200° C.
in the presence of at least one catalyst (F) selected from the group consisting of
(F1) tertiary amines and amidines,
(F2) basic alkali metal salts, alkaline earth metal salts or quaternary ammonium salts, and
(F3) alkoxides, alkanoates, chelates or organometallic compounds of metals from groups IIIA to VIIIA or IB to VB in the Periodic Table of the Elements.

With the process of the invention it is possible to prepare noncrosslinked hyper-branched polylysines having a weight-average molecular weight $M_w$ of up to 750 000 Da, preferably up to 700 000 Da, more preferably up to 650 000 Da, very preferably up to 600 000 Da, and in particular up to 550 000 Da.

Through the reaction regime of the invention it is also possible for the first time to prepare noncrosslinked hyper-branched polylysines having a weight-average molecular weight $M_w$ of more than 5000 Da, preferably more than 7500 Da, more preferably more than 10 000 Da, very preferably more than 12 000 Da, in particular more than 15 000 Da, especially more than 20 000 Da, and even more than 25 000 Da, and these polylysines are likewise provided by the present invention.

Such polylysines of the invention, synthesized exclusively from component (A) with component (B), if appropriate, are notable for a water-solubility at 50° C. of more than 90% by weight for a molar weight of 5000 Da, preferably more than 6000 Da, and more preferably more than 7000 Da.

The glass transition temperature $T_g$, determined in accordance with ASTM specification D3418-03 via differential scanning calorimetry, amounts in general to from −20 to 100° C., preferably from −10 to 80° C., and more preferably from 0 to 60° C.

The term "noncrosslinked" means, in accordance with the invention, that the polylysines obtained inventively from a salt (A) of lysine with at least one acid exhibit a lower degree of crosslinking than polylysines of the same weight-average molecular weight $M_w$ that have been obtained by polymerization of free lysine base.

One measure for this is, for example, a comparison of the gel content of the poly-lysines, i.e., the polylysine fraction which is insoluble when stored at room temperature (23° C.) under water for 24 hours, divided by the total amount of the sample, and multiplied by 100.

For polylysines of the invention the gel content is generally not more than 20% as compared with polylysines obtained by polymerizing free lysine base, preferably not more than 10%, and more preferably not more than 5%.

Modified polylysines, furthermore, are provided by the present invention.

The reaction of the invention is carried out in general at a temperature from 120 to 200° C., preferably 130 to 180° C., and more preferably 150 to 170° C., and very preferably 150 to 160° C.

The pressure at which the reaction is carried out plays a minor part. If a solvent (E) is used that has a lower boiling point than the desired reaction temperature then it is sensible to apply pressure in order that the desired reaction temperature can be attained.

The reaction time varies according to the desired molecular weight and amounts in general to at least one hour, preferably at least 2 hours, more preferably at least 4 hours, very preferably at least 6 hours, and in particular at least 8 hours. In general the reaction is over after not more than 72 hours, preferably after not more than 60 hours, more preferably after not more than 48 hours, and very preferably after not more than 36 hours.

The higher the desired molecular weight of the polylysines the longer, in general, the reaction time that must be chosen.

The reaction can be carried out continuously or, preferably, batchwise. The lysine reactant can be either included in its entirety in the initial charge or else added, slowly, continuously to the reactor. The latter mode is also referred to as slow monomer addition. The reaction is preferably carried out in what is called a one-pot mode, in which the monomer is included in its entirety in the initial charge and the reaction is carried out in a reactor with backmixing. Also conceivable, however, are reaction regimes in a multistage reactor system, a stirred-tank cascade for example, or in a tube reactor. In one preferred alternative embodiment of the present invention the reaction can be carried out in a compounder, extruder, intensive mixer or paddle dryer.

The reaction may, if appropriate, also be carried out with the assistance of ultrasound or of microwave radiation.

The individual components can be introduced at the beginning of the reaction regime or added in staggered form, depending on the stage of polymer formation at which it is desired to incorporate the respective reaction components into the polymer.

In accordance with the invention lysine is used in the form of a salt (A) of the free lysine base with an acid, preferably an acid having a $pK_a$ of less than 2.2, more preferably a strong acid.

Examples of acids are acetic acid, formic acid, carbonic acid, glycolic acid, propionic acid or lactic acid.

Examples of acids having $pK_a$ of less than 2.2 include for example phosphoric acid ($H_3PO_4$), phosphorous acid ($H_3PO_3$), pyrophosphoric acid ($H_4P_2O_7$) or hydrogen sulfate ($HSO_4^-$).

Examples of strong acids are sulfuric acid ($H_2SO_4$), perchloric acid, hydrochloric acid, and hydrobromic acid.

Very particular preference is given to sulfuric acid and hydrochloric acid, especially hydrochloric acid.

The formation of an inner salt for lysine is not included here as salt formation; the acid must be an acid other than lysine.

A further possibility is to use the salt of lysine in the form of any desired hydrate. It is irrelevant for the purposes of the invention which hydrate is employed.

Since lysine has two amino groups it is possible to employ, based on the amount of lysine, preferably more than 50 mol %, more preferably 50 to 200 mol %, very preferably 75 to 200 mol %, and in particular 100 to 200 mol % of acid for salt formation.

If appropriate, albeit it less preferably, the carboxy group of the lysine can also be present in the form of an ester, for example, a $C_1$-$C_{10}$ alkyl ester, preferably a $C_1$-$C_4$ alkyl ester.

Lysine can be used in enantiomerically pure form or as a racemate, preferably as a racemate or in the form of L-lysine, more preferably in the form of L-lysine.

It will be appreciated that L-lysine can be also be copolymerized with other amino acids (B). Mention may be made here, for example, of glycine, alanine, β-alanine, valine, leucine, isoleucine, tert-leucine, phenylalanine, tyrosine, tryptophan, proline, aspartic acid, glutamic acid, asparagine, glutamine, serine, threonine, cysteine, methionine, arginine, histidine, 4-aminobutyric acid, cystine, citrulline, theanine, homocysteine, 4-hydroxyproline, alliin or ornithine.

Amino acids (B) in this context are amino acids which have at least one primary or secondary amino group and at least one carboxyl group.

Additionally it is possible as well for the noncrosslinked hyperbranched polylysines to be randomly or block-copolymerized with carboxylic acids (C) or amines (D), in which case it should be ensured that the overall molar ratio of amino groups to carboxyl groups in the reaction mixture is between 3:1 to 1:3, preferably 3:1 to 1:2, more preferably 3:1 to 1:1, and very preferably 2.5:1 to 1.5:1.

Dicarboxylic and polycarboxylic acids (C) suitable for this copolymerization typically have at least 2, preferably 2 to 4, more preferably 2 to 3, and very preferably 2 carboxyl groups. Preferred dicarboxylic and polycarboxylic acids (C) comprise 2 to 30 carbon atom atoms and can be aliphatic, cycloaliphatic or aromatic.

Examples of suitable dicarboxylic acids include the following: oxalic acid, malonic acid, succinic acid, glutaric acid, adipic acid, pimelic acid, suberic acid, azelaic acid, sebacic acid, undecane-α,ω-dicarboxylic acid, dodecane-α,ω-dicarboxylic acid, cis- and trans-cyclohexane-1,2-dicarboxylic acid, cis- and trans-cyclohexane-1,3-dicarboxylic acid, cis- and trans-cyclohexane-1,4-dicarboxylic acid, cis- and trans-cyclopentane-1,2-dicarboxylic acid, and cis- and trans-cyclopentane-1,3-dicarboxylic acid, it being possible for the dicarboxylic acids to be substituted by one or more radicals selected from:

$C_1$-$C_{10}$ alkyl groups, examples being methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, 2-ethylhexyl, n-nonyl or n-decyl, $C_3$-$C_{12}$ cycloalkyl groups, examples being cyclopropyl, cyclobutyl, cyclopentyl, cyclo-hexyl, cycloheptyl, cyclooctyl, cyclononyl, cyclodecyl, cycloundecyl and cyclododecyl; preference is given to cyclopentyl, cyclohexyl and cycloheptyl, alkylene groups such as methylene or ethylidene, and/or $C_6$-$C_{14}$ aryl groups such as, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl, preferably phenyl, 1-naphthyl, and 2-naphthyl, more preferably phenyl.

Examples that may be mentioned of substituted dicarboxylic acids include the following: 2-methylmalonic acid, 2-ethylmalonic acid, 2-phenylmalonic acid, 2-methyl-succinic acid, 2-ethylsuccinic acid, 2-phenylsuccinic acid, itaconic acid, and 3,3-dimethylglutaric acid.

Also suitable are aromatic dicarboxylic acids such as, for example phthalic acid, isophthalic acid or terephthalic acid.

Examples of suitable tricarboxylic and tetracarboxylic acids include trimesic acid, trimellitic acid, pyromellitic acid, butanetricarboxylic acid, naphthalenetricarboxylic acid, and cyclohexane-1,3,5-tricarboxylic acid.

Excluded from consideration as component (C) are those dicarboxylic or polycarboxylic acids which have activated double bonds, such as α,β-ethylenically unsaturated double bonds, for example, and/or amino acids (B).

Preferred components (C) are those dicarboxylic or polycarboxylic acids which apart from carboxyl groups contain no further functional groups.

It is additionally possible to use mixtures of two or more of the aforementioned carboxylic acids. The carboxylic acids can be used either as such or in the form of derivatives. Such derivatives are, in particular, the anhydrides of the aforementioned carboxylic acids, in either monomeric or polymeric form;

the esters of the aforementioned carboxylic acids, such as monoalkyl or dialkyl esters, preferably $C_1$ to $C_4$-alkyl esters, more preferably monomethyl or dimethyl esters or the corresponding monoethyl or diethyl esters, but also the monoalkyl and dialkyl esters derived from higher alcohols such as, for example n-propanol, isopropanol, n-butanol, isobutanol, tert-butanol, n-pentanol, and n-hexanol, monovinyl and divinyl esters, and mixed esters, preferably methyl ethyl esters.

It is also possible to use a mixture of a carboxylic acid and one or more of its derivatives, or a mixture of two or more different derivatives of one or more dicarboxylic acids.

Particular preference is given to using, as carboxylic acid, succinic acid, glutaric acid, adipic acid, phthalic acid, isophthalic acid, terephthalic acid or their monomethyl or dimethyl esters.

Suitable amines (D) have typically at least 2, preferably 2 to 6, more preferably 2 to 4 amino groups, having generally 2 to 30 carbon atoms, and can be aliphatic, cycloaliphatic or aromatic. The amines (D) have primary and/or secondary amino groups.

Suitable diamines are preferably those of the formula $R^1$—NH—$R^2$—NH—$R^3$ in which $R^1$ and $R^3$ independently of one another are hydrogen or an alkyl radical, cycloalkyl radical, aryl radical or arylalkyl radical having 1 to 20 carbon atoms. The alkylene radical $R^2$ may be linear or else cyclic.

Examples of preferred diamines are ethylenediamine, the propylenediamines (1,2-diaminopropane and 1,3-diaminopropane), N-methylethylenediamine, piperazine, tetramethylenediamine (1,4-diaminobutane), N,N'-dimethylethylenediamine, N-ethylethylenediamine, 1,5-diaminopentane, 1,3-diamino-2,2-diethylpropane, 1,3-bis(methylamino)propane, hexamethylenediamine (1,6-diaminohexane), heptanediamine, octanediamine, nonanediamine, decanediamine, dodecanediamine, hexadecanediamine, tolylenediamine, xylylenediamine, diaminodiphenylmethane, diaminodicyclohexylmethane, phenylenediamine, cyclohexylenediamine, bis(aminomethyl)cyclohexane, diaminodiphenyl sulfone, 1,5-diamino-2-methylpentane, 3-(propylamino)propylamine, N,N'-bis(3-aminopropyl)piperazine, N,N'-bis(3-amino-propyl)piperazine, isophoronediamine (IPDA), 3(or 4),8(or 9)-bis(aminomethyl)-tricyclo[$5.2.1.0^{2,6}$]decane isomer mixtures, 2-butyl-2-ethyl-1,5-pentamethylenediamine, 2,2,4- or 2,4,4-trimethyl-1,6-hexamethylenediamine, 2-aminopropylcyclohexylamine, 3(4)-aminomethyl-1-methylcyclohexylamine, 1,4-diamino-4-methylpentane, amine-terminated polyoxyalkylene polyols (so-called Jeffamines) or amine-terminated polytetramethylene glycols.

Preference is given to butylenediamine, pentanediamine, hexamethylenediamine, tolylenediamine, xylylenediamine, diaminodiphenylmethane, diaminodicyclo-hexylmethane, phenylenediamine, cyclohexylenediamine, diaminodiphenyl sulfone, isophoronediamine, bis(aminomethyl)cyclohexane, amine-terminated polyoxyalkylene polyols (so-called Jeffamines) or amine-terminated polytetramethylene glycols.

Examples of suitable amines having three or more reactive primary and/or secondary amino groups are tris(aminoethyl)amine, tris(aminopropyl)amine, tris(aminohexyl)-amine, trisaminohexane, 4-aminomethyl-1,8-octanediamine, trisaminononane, bis(aminoethyl)amine, bis(aminopropyl)amine, bis(aminobutyl)amine, bis(aminopentyl)-amine, bis(aminohexyl)amine, N-(2-aminoethyl)propanediamine, melamine, oligomeric diaminodiphenylmethanes (polymer-MDA), N,N'-bis(3-aminopropyl)ethylenediamine, N,N'-bis(3-aminopropyl)butanediamine, N,N,N',N'-tetra(3-aminopropyl)ethylenediamine, N,N,N',N'-tetra(3-aminopropyl)butylenediamine, amine-terminated polyoxyalkylene polyols having a functionality of three or more (so-called Jeffamines), polyethylene-imines having a functionality of three or more, or polypropyleneimines having a functionality of three or more.

Preferred amines having three or more reactive primary and/or secondary amino groups are tris(aminoethyl)amine, tris(aminopropyl)amine, tris(aminohexyl)amine, trisaminohexane, 4-aminomethyl-1,8-octanediamine, trisaminononane, bis(aminoethyl)-amine, bis(aminopropyl)amine, bis(aminobutyl)amine, bis(aminopentyl)amine, bis(aminohexyl)amine, N-(2-aminoethyl)propanediamine, melamine or amine-terminated polyoxyalkylene polyols having a functionality of three or more (so-called Jeffamines).

Particular preference is given to amines having three or more primary amino groups, such as tris(aminoethyl)amine, tris(aminopropyl)amine, tris(aminohexyl)amine, trisaminohexane, 4-aminomethyl-1,8-octanediamine, trisaminononane or amine-terminated polyoxyalkylene polyols having a functionality of three or more (so-called Jeffamines).

It is also possible to use mixtures of two or more carboxylic acids and/or carboxylic acid derivatives, or mixtures of two or more amines. The functionality of the various carboxylic acids or amines may be the same or different.

The reaction of the lysine (A) and, if appropriate, of the additional monomers (B) to (D) can optionally take place in a solvent (E). In this context it is possible in general to use all solvents, preferably those which are inert toward the respective reactants under the reaction conditions. It is preferred to operate in organic solvents, such as decane, dodecane, benzene, toluene, chlorobenzene, dichlorobenzene, xylene, dimethyl-formamide, dimethylacetamide or solvent naphtha. Also conceivable and additionally preferred, however, are water and alkanols having 1 to 10 carbon atoms, especially methanol, ethanol, isopropanol, n-butanol, and 2-ethylhexanol.

In one preferred embodiment of the process of the invention the reaction is carried out in bulk, in other words without solvent.

It is also possible, however, for minor amounts of water to be present: for example, up to 20% by weight, preferably up to 15%, more preferably up to 10%, and very preferably up to 5% by weight, with respect to the salt of lysine.

The water liberated during the reaction can be separated off by distillation, if appropriate with passage over the liquid phase of a gas which is inert under the reaction conditions, with passage through the liquid phase of a gas which is inert under the reaction conditions, if appropriate under reduced pressure, and in this way said water can be removed from the reaction equilibrium. This also has the effect of accelerating the reaction.

Gases inert under the reaction conditions may be, for example, noble gases, such as helium or argon, for example, nitrogen, carbon monoxide or carbon dioxide.

The reaction is accelerated by adding catalysts (F) or catalyst mixtures.

Suitable catalysts are compounds which catalyze esterification or amidation and are selected from the group of (F1) tertiary amines and amidines, (F2) basic alkali metal salts, alkaline earth metal salts or quaternary ammonium salts, and (F3) alkoxides, alkanoates, chelates or organometallic compounds of metals from groups IIIA to VIIIA or IB to VB in the Periodic Table of the Elements.

Tertiary amines and amidines (F1) are those which have no free hydrogen atoms on the amino groups but whose nitrogen atoms are instead connected via three bonds exclusively to carbon atoms. Preferred tertiary amines and amidines are those having a pK$_b$ of more than 8.9, more preferably more than 10.3. With very particular preference the tertiary amines and amidines have only low volatility at the reaction temperature, and in particular have a boiling point above the reaction temperature.

Examples of tertiary amines are trioctylamine, tridodecylamine, tribenzylamine, N,N,N',N'-tetramethylethylenediamine, 1-methylpyrrole, pyridine, 4-dimethylamino-pyridine, picoline, N,N'-dimethylpiperazine, N-methylmorpholine, N-methylpiperidine, N-ethylpiperidine, N,N-dimethylaniline, N,N-dimethylbenzylamine, 1,4-diazabicyclo-[2.2.2]octane, 1,5-diazabicyclo[4.3.0]non-5-ene or 1,8-diazabicyclo[5.4.0]undec-7-ene. Examples of amidines are imidazoles, such as N-methylimidazole, imidazole, 1-methyl-imidazole, 2-methylimidazole or 1,2-dimethylimidazole.

The basic alkali metal, alkaline earth metal or quaternary ammonium salts (F2) are hydroxides, oxides, carbonates, hydrogen carbonates, $C_1$-$C_{10}$ alkoxides or $C_1$-$C_{10}$ alkanoates with cations from the series of the alkali metals or alkaline earth metals or quaternary ammonium ions.

Alkali metals are preferably Li, Na, K or Cs, more preferably Na and K. Alkaline earth metals are preferably Mg and Ca. Quaternary ammonium ions can have 4 to 32 carbon atoms and be substituted by alkyl, cycloalkyl, aryl or arylalkyl, preferably by alkyl or arylalkyl, and more preferably by alkyl.

Preferred $C_1$-$C_{10}$ alkoxides are $C_1$-$C_4$ alkoxides, more preferably methoxide, ethoxide, isopropoxide, and n-butoxide, very preferably methoxide and ethoxide, and especially methoxide.

Preferred $C_1$-$C_{10}$ alkanoates are $C_1$-$C_4$ alkanoates, particular preference being given to acetate.

Preferred compounds (F2) are lithium, sodium, potassium or cesium hydroxide, lithium, sodium, potassium or cesium carbonate, lithium, sodium, potassium or cesium acetate, particular preference being given to sodium or potassium hydroxide.

Compounds (F3) are alkoxides, alkanoates, chelates or organometallic compounds of metals from groups IIIA to VIIIA or IB to VB in the Periodic Table of the Elements.

Examples of alkoxides are $C_1$-$C_{10}$ alkoxides, preferably $C_1$-$C_4$ alkoxides, more preferably methoxide, ethoxide, isopropoxide, and n-butoxide, very preferably methoxide and ethoxide, and especially methoxide.

Examples of alkanoates are $C_1$-$C_{20}$ alkanoates, preferably $C_1$-$C_4$ alkanoates, particular preference being given to acetate.

Chelates are cyclic compounds in which metals and moieties with lone electron pairs form a ring. A preferred chelate former is acetylacetonate.

Organometallic compounds are those having a direct metal-carbon bond.

Preferred metals are boron, aluminum, tin, zinc, titanium, antimony, zirconium or bismuth.

Preferred compounds (F3) are titanium tetrabutoxide, titanium tetraisopropoxide, zirconium acetylacetonate, zirconium tetrabutoxide, tin(II) n-octanoate, tin(II) 2-ethylhexanoate, tin(II) laurate, dibutyltin oxide, dibutyltin dichloride, dibutyltin diacetate, dibutyltin dilaurate, dibutyltin dimaleate, dioctyltin diacetate, antimony triethoxide or boronic acid derivatives—for example, pyridineboronic acid.

Preferred catalysts are (F1) and (F2), particular preference being given to compounds (F2).

The compounds (A) to (E) are reacted with one another, for the reaction of the invention, in the following proportions:

(B) up to 100 mol % based on (A), preferably 0 to 75 mol %, more preferably 0-50 mol %, very preferably 0-25 mol %, in particular 0-15 mol %, and especially 0 mol %, (C) 0 to 50 mol % based on (A), preferably 0 to 30 mol %, more preferably 0-25 mol %, very preferably 0-10 mol %, in particular 0-5 mol %, and especially 0 mol %.

(D) 0 to 50 mol % based on (A), preferably 0 to 30 mol %, more preferably 0-25 mol %, very preferably 0-10 mol %, in particular 0-5 mol %, and especially 0 mol %, (E) 0-200% by weight with respect to the sum of components (A) to (D), preferably 0-100%, more preferably 0-75%, very preferably 0-50%, in particular 0-25%, and especially 0% by weight, and (F1) or (F2) up to 110 mol %, preferably up to 105 mol %, more preferably up to 100 mol %, and generally at least 80 mol % with respect to the acid which forms the salt with lysine, and/or (F3) 0.1 to 20 mol % with respect to the sum of components (A) to (D), and preferably 0.1 to 15 mol %.

After the reaction, in other words without additional modification, the high-functionality highly branched polypeptides prepared by the process of the invention are terminated by amino and/or carboxyl groups. They dissolve readily in polar solvents, for example in water, alcohols, such as methanol, and in modified form also in ethanol, butanol, alcohol/water mixtures, dimethylformamide, dimethylacetamide, N-methylpyrrolidone, chloroform, ethylene carbonate or propylene carbonate.

A high-functionality polypeptide for the purposes of the invention is a product which has at least three, preferably at least six, and in particular at least ten functional groups. In principle there is no upper limit on the number of functional groups, although products having a very large number of functional groups may exhibit unwanted properties, such as high viscosity or a poor solubility. The high-functionality polypeptides of the present invention generally contain not more than 200 functional groups, preferably not more than 100 functional groups. By functional groups here are meant primary, secondary or tertiary amino groups or carboxyl groups. In addition the high-functionality highly branched polypeptide may have further functional groups which do not participate in the synthesis of the highly branched polymer (see below). These further functional groups may be introduced by means of diamines or polyamines, or dicarboxylic or polycarboxylic acids, which in addition to primary and secondary amino groups, or acid groups, also contain further functional groups.

In one further preferred embodiment the polypeptides of the invention may comprise further functional groups. The functionalization in this case can take place during the reaction, i.e., during the polycondensation reaction that brings about the increase in molecular weight, or else after the end of the polycondensation reaction, by subsequent functionalization of the resulting polypeptides.

If, before or during the molecular weight increase, components are added which in addition to amino and/or carboxyl groups have further functional groups, then a polypeptide is obtained which has, randomly distributed, further functional groups—that is, functional groups other than the amino or carboxyl groups.

By way of example, before or during the polycondensation, it is possible to add components (G), which have either primary or secondary amino groups or carboxyl groups, hydroxyl groups, mercapto groups, tertiary amino groups, ether groups, urea groups, sulfonic acid groups, phosphonic acid groups, silane groups, siloxane groups, aryl radicals or short-chain or long-chain, linear or branched alkyl radicals which if appropriate are also partly fluorinated or perfluorinated.

Hydroxyl-containing components (G) which can be added for functionalization comprise, for example, ethanolamine, N-methylethanolamine, propanolamine, isopropanolamine, butanolamine, 2-amino-1-butanol, 2-(butylamino)ethanol, 2-(cyclohexylamino)ethanol, 2-(2'-aminoethoxy)ethanol or higher alkoxylation products of ammonia, or 4-hydroxypiperidine, 1-hydroxyethylpiperazine, diethanolamine, dipropanolamine, diisopropanolamine, tris(hydroxymethyl)aminomethane or tris(hydroxyethyl)aminomethane, and also dimethylolpropionic acid, dimethylolbutyric acid, hydroxypivalic acid, lactic acid or glycolic acid.

Mercapto-comprising components which can be added for functionalization comprise, for example, cysteamine, mercaptoacetic acid or mercaptoethanol. With tertiary amino groups the highly branched polypeptides can be functionalized by, for example, concomitant use of di(aminoethyl)methylamine, di(aminopropyl)methylamine or N,N-dimethylethylenediamine. With ether groups the highly branched polypeptides can be functionalized by concomitant use of amine-terminated polyetherols (so-called Jeffamines) or with polyether-carboxylic acids. With sulfonic or phosphonic acid groups the highly branched polypeptides can be functionalized by, for example, concomitant use of aminosulfonic acids or aminophosphonic acids. With groups comprising silicon the highly branched polypeptides can be functionalized by concomitant use of hexamethyldisilazane, N-(3-trimethylsilylethyl)ethylenediamine, 3-aminopropyl-trimethylsiloxane, 3-aminopropyltriethylsiloxane, 3-isocyanatopropyltrimethylsiloxane or 3-isocyanatopropyltriethylsiloxane. With long-chain alkyl radicals the highly branched polypeptides can be functionalized by concomitant use of alkylamines, alkylcarboxylic acids, alkylsulfonic acids or alkyl isocyanates.

The polypeptides can also be functionalized, additionally, through the use of small amounts of monomers (H) which do not have amino groups and do not have carboxyl groups but instead have functional groups which are different from amino groups or carboxyl groups but are able to react with amino or carboxyl groups. Mention may be made here, by way of example, of alcohols having a functionality of two, three or more, which can be incorporated into the polypeptide via ester functions. Thus, for example, hydrophobic properties can be achieved through the addition of long-chain alkanediols, while polyethylene oxide diols or triols produce hydrophilic properties in the polypeptide.

The stated functional groups other than amine or carboxylic acid groups that are introduced before or during the polycondensation are introduced generally in amounts of 0.1 to 80 mol %, preferably in amounts of 1 to 50 mol %, based on the sum of the amino groups and carboxylic acid groups.

The present invention further provides modified polylysines in which the accessible amino and/or carboxyl groups have been at least partly further modified, i.e., reacted with reagents which alter the properties of the polylysine thus modified. Examples of these properties include solubility, dispersibility, hydrophilicity, hydrophobicity, and rheology.

The polylysines are modified preferably with the polylysines of the invention, as described above, whose preparation is based on the reaction of a salt of lysine with an acid. Also conceivable, however, is the modification of polylysines obtained in any desired way, having been prepared, for example, by polymerization or copolymerization of lysine-containing reactants other than (A)—free lysine base, for example.

The polylysines which can be employed for such modification ought to have a weight-average molecular weight $M_w$ or more than 1000 Da, preferably more than 1500 Da, more preferably more than 2000 Da, very preferably more than 2500 Da, in particular 3000 Da, and especially 5000 Da. With advantage it is also possible to use polylysines which have an $M_w$ or more than 7500 Da, more than 10 000 Da, more than 15 000 Da, or even more than 20 000 Da.

An upper limit on the weight-average molecular weight $M_w$ is not essential to the invention. It is possible to use, for example, polylysines having an $M_w$ up to 750 000 Da, preferably up to 600 000 Da, more preferably up to 500 000 Da, very preferably up to 400 000 Da, and in particular up to 300 000 Da.

The polylysines which can be employed may for example comprise primary, secondary or tertiary, free or protonated amino groups, calculated as $NH_2$, in an amount of 1% to 21.9% by weight, preferably 3% to 18% by weight.

The polylysines which can be employed may for example have a free or deprotonated acid group content, calculated as COOH, of 0 to 30% by weight and preferably 0 to 15% by weight.

Subsequent functionalization of high-functionality highly branched polypeptides comprising amino groups can be achieved for example by addition of molecules without amino groups or carboxyl groups (I) but comprising acid groups, isocyanate groups, keto groups or aldehyde groups, or activated double bonds, examples being molecules comprising acrylic double bonds. By way of example it is possible to obtain polypeptides comprising acid groups by reaction with acrylic acid or maleic acid and derivatives thereof, esters for example, with subsequent hydrolysis, if appropriate.

Additionally it is possible to convert high-functionality polypeptides comprising amino groups into high-functionality polypeptide polyols by reaction with alkylene oxides (J1), such as ethylene oxide, propylene oxide or butylene oxide, for example.

A further possibility for the functionalization of the amino groups in the high-functionality polypeptides lies in the at least partial reaction of the amino groups with lactones and/or lactams, to form polyester chains with a terminal hydroxyl group which start out from these amino groups. Exemplary lactams are ε-caprolactam, δ-valerolactam, γ-butyrolactam, N-methylcaprolactam, and N-methylpyrrolidone. Exemplary lactones are ε-caprolactone, δ-valerolactone, and γ-butyrolactone.

A further possibility of preparing polypeptide/polyether compounds lies in the reaction of the polypeptides with polyalkylene oxides (J2) which are terminated by amino groups or acid groups and have a functionality of one, two or more, preferably polyethylene oxides, polypropylene oxides or polyethylene-propylene oxides.

By salt formation with protic acids or by quaternization of the amino functions with alkylating reagents (K), such as methyl halides, alkyl tosylates or dialkyl sulfates, the high-functionality, highly branched polypeptides can be made soluble in water or dispersible in water.

The salt formation can also be carried out by mixing or reacting the amino groups of the hyperbranched polymers of the invention stoichiometrically or substoichiometrically with acidic components or salts thereof that have long-chain linear or branched alkyl radicals, cycloalkyl radicals substituted if appropriate, or aryl radicals substituted if appropriate, and which are commonly known as soaps or surfactants.

Acidic components of this kind may preferably contain at least one, with particular preference precisely one, carboxyl, sulfonic acid, sulfate or phosphonic acid group.

The hyperbranched polymers may for example be reacted with alkyl- or alkenylcarboxylic acids, such as, for example, octanoic acid, nonanoic acid, decanoic acid, dodecanoic acid, hexadecanoic acid, stearic acid, oleic acid, linoleic acid, linolenic acid or their Li, Na, K, Cs, Ca or ammonium salts, with alkylsulfonic acids, examples being octanesulfonic acid, dodecanesulfonic acid, stearylsulfonic acid or oleylsulfonic acid, or their Li, Na, K, Cs, Ca or ammonium salts, with camphorsulfonic acid, cyclododecylsulfonic acid, p-toluenesulfonic acid, benzenesulfonic acid, 4-hexyl-benzenesulfonate, 4-octylbenzenesulfonate, 4-decylbenzenesulfonate or 4-dodecyl-benzenesulfonate or their Li, Na, K, Cs, Ca or ammonium salts, or with alkyl sulfates, examples being n-alkyl sulfates or secondary alkyl sulfates. This produces ionic polylysine-surfactant complexes which, for example, have liquid-crystalline properties or may act as polymeric ionic liquids.

The alkyl, cycloalkyl or aryl radicals may in this case have up to 20 carbon atoms, preferably 6 to 20, more preferably 7 to 20.

In order to achieve water repellency (hydrophobicity) it is possible for amine-terminated, high-functionality, highly branched polypeptides to be reacted with saturated or unsaturated long-chain carboxylic acids (L), with amino-reactive derivatives thereof, or else with aliphatic or aromatic isocyanates, trialkylsilyl halides, partly or fully fluorinated alcohols, alkyl halides, carboxylic acids or amines. Polypeptides terminated by carboxylic acid groups can be hydrophobicized by reaction with long-chain alkylamines or long-chain aliphatic monoalcohols.

In order to achieve nonionic hydrophilicization it is possible to react amine-terminated, high-functionality, highly branched polypeptides with aliphatic or aromatic isocyanates that additionally comprise polyethylene glycol chains.

Polypeptides terminated by carboxylic acid groups can be nonionically hydrophilicized by reaction with long-chain, preferably monofunctional polyethylene glycols or polyethylene glycol amines (Jeffamines).

In order to achieve an amphiphilic character the high-functionality, highly branched polypeptides can also be modified with hydrophobic and hydrophilic agents simultaneously—for example, with long-chain aliphatic carboxylic acids, alcohols, amines or isocyanates which have a functionality of one, two or more, and at the same time with alcohols, amines, acids or isocyanates which contain polyethylene glycol chains and have a functionality of one, two or more.

For purification, specifically also for the separation of the inorganic salts that form during the preparation, the polymers of the invention can be dissolved, for example, in polar or apolar solvents, the salts not going into solution and being separable from the polymer by filtration. By way of example mention may be made here of the dissolution of the unmodified polylysine in ethanol, where the potassium chloride formed in the reaction was precipitated as a sediment and could be separated from the polymer solution by filtration.

The present invention also provides for the use of the high-functionality highly branched polypeptides of the invention as adhesion promoters and thixotropic agents, solubilizers, phase transfer reagents for water-insoluble chemicals, phase transfer reagents for water-soluble chemicals, surface modifiers, and components in the production of printing inks, paints, coatings, adhesives, sealants, corrosion control products, casting elastomers, and foams.

EXAMPLES

Example 1

Condensation Product of L-Lysine*1HCl, Reaction at 150° C. with NaOH Added, without Reduced Pressure L-Lysine*HCl (11 g, 60 mmol) and solid NaOH (2.4 g, 60 mmol) were triturated in a mortar and the mixture was subsequently heated in a Schlenk tube at 150° C. During the reaction, samples were taken after 14, 24, 38, and 48 hours, dissolved in water, the solution was filtered, and the molecular weights were determined by GPC analysis. The GPC analysis took place on untreated samples, taken directly from the reaction mixture, by means of a column combination comprising OHpak SB-803 HQ and SB-804 HQ (Shodex) in aqueous solution with the addition of 0.1 mol/l sodium hydrogen carbonate at 30° C., with a flow rate of 0.5 ml/min and with polyethylene oxide as standard. Detection took place using a UV detector which operated at a wavelength of 230 nm.

TABLE 1

Polycondensation of L-lysine*HCl at 150° C. with NaOH added

| Reaction time | Molecular weight (Mw) | Polydispersity |
|---|---|---|
| 14 hours | 2500 g/mol | 2.2 |
| 24 hours | 3400 g/mol | 2.4 |
| 38 hours | 14 600 g/mol | 5 |
| 48 hours | 28 100 g/mol | 9.3 |

Example 2

Condensation Product of L-Lysine*HCl, Reaction at 150° C. with KOH Added, without Reduced Pressure L-Lysine*HCl (11 g, 60 mmol) and KOH (3.3 g, 60 mmol) were triturated in a mortar and the mixture was subsequently heated in a Schlenk tube at 150° C. During the reaction, samples were taken after 14, 24, 38, and 48 hours, dissolved in water, the solution was filtered, and the molecular weights were determined as described in Example 1 (see Table 2).

TABLE 2

Polycondensation of L-lysine*HCl at 150° C. with KOH added

| Reaction time | Molecular weight (Mw) | Polydispersity |
|---|---|---|
| 14 hours | 3300 g/mol | 2.8 |
| 24 hours | 9900 g/mol | 4.9 |
| 38 hours | 36 100 g/mol | 11.3 |
| 48 hours | 283 700 g/mol | 61.8 |

Example 3

Condensation Product of L-Lysine*HCl, Reaction at 150° C. with NaOH and Zirconium(IV)Butoxide Added, without Reduced Pressure L-Lysine*HCl (11 g, 60 mmol) and NaOH (2.4 g, 60 mmol) were triturated in a mortar and the mixture, following addition of 1 ml of zirconium(IV)butoxide (Zr(Bu)$_4$), was heated in a Schlenk tube at 150° C. During the reaction, samples were taken after 14, 24, 38, and 48 hours, dissolved in water, the solution was filtered, and the molecular weights were determined by GPC as described in Example 1 (see Table 3).

TABLE 3

Polycondensation of L-lysine*HCl at 150° C. with NaOH and zirconium(IV) butoxide added

| Reaction time | Molecular weight (Mw) | Polydispersity |
|---|---|---|
| 14 hours | 3100 g/mol | 2.0 |
| 24 hours | 7700 g/mol | 2.8 |
| 38 hours | 25 700 g/mol | 5.5 |
| 48 hours | 57 300 g/mol | 10.4 |

Example 4

Condensation Product of L-Lysine*HCl, Reaction at 150° C. with KOH and Zirconium(IV)Butoxide Added, without Reduced Pressure L-Lysine*HCl (11 g, 60 mmol) and KOH (3.3 g, 60 mmol) were triturated in a mortar and the mixture, following addition of 1 ml of zirconium(IV)butoxide (Zr(OBu)$_4$), was heated in a Schlenk tube at 150° C. During the reaction, samples were taken after 14, 24, 38, and 48 hours, dissolved in water, the solution was filtered, and the molecular weights were determined by GPC as described in Example 1 (see Table 4).

TABLE 4

Polycondensation of L-lysine*HCl at 150° C. with KOH and zirconium(IV) butoxide added

| Reaction time | Molecular weight (Mw) | Polydispersity |
|---|---|---|
| 14 hours | 4900 g/mol | 2.5 |
| 24 hours | 19 400 g/mol | 4.6 |
| 38 hours | 139 000 g/mol | 23 |
| 48 hours | 510 000 g/mol | 107 |

Example 5

Condensation Product of L-Lysine*HCl, Reaction at 150° C. with NaOH and Dibutyltin Dilaurate Added, without Reduced Pressure L-Lysine*HCl (11 g, 60 mmol) and NaOH (2.4 g, 60 mmol) were triturated in a mortar and the mixture, following addition of 1 ml of dibutyltin dilaurate, was heated in a Schlenk tube at 150° C. During the reaction, samples were taken after 14, 24, 38, and 48 hours, dissolved in water, the solution was filtered, and the molecular weights were determined by GPC as described in Example 1 (see Table 5).

TABLE 5

Polycondensation of L-lysine*HCl at 150° C. with NaOH and dibutyltin dilaurate added

| Reaction time | Molecular weight (Mw) | Polydispersity |
|---|---|---|
| 14 hours | 2300 g/mol | 2.5 |
| 24 hours | 5300 g/mol | 4.1 |

TABLE 5-continued

Polycondensation of L-lysine*HCl at 150° C. with NaOH and dibutyltin dilaurate added

| Reaction time | Molecular weight (Mw) | Polydispersity |
|---|---|---|
| 38 hours | 37 000 g/mol | 21.2 |
| 48 hours | 49 400 g/mol | 27.9 |

Example 6

Condensation Product of L-Lysine*HCl, Reaction at 150° C. with NaOH and Triphenyl Phosphite Added, without Reduced Pressure L-Lysine*HCl (11 g, 60 mmol) and NaOH (2.4 g, 60 mmol) were triturated in a mortar and the mixture, following addition of 1 ml of triphenyl phosphite, was heated in a Schlenk tube at 150° C. During the reaction, samples were taken after 14, 24, 38, and 48 hours, dissolved in water, the solution was filtered, and the molecular weights were determined by GPC as described in Example 1 (see Table 6).

TABLE 6

Polycondensation of L-lysine*HCl at 150° C. with NaOH and triphenyl phosphite added

| Reaction time | Molecular weight (Mw) | Polydispersity |
|---|---|---|
| 14 hours | 3200 g/mol | 3.2 |
| 24 hours | 6400 g/mol | 4.6 |
| 38 hours | 14 000 g/mol | 8.7 |
| 48 hours | 18 400 g/mol | 12.7 |

Example 7

Condensation Product of L-Lysine*HCl, Reaction at 180° C. with NaOH Added, without Reduced Pressure L-Lysine*HCl (5.5 g, 30 mmol) and NaOH (1.2 g, 30 mmol) were triturated in a mortar and the mixture was subsequently heated in a Schlenk tube at 180° C. After 24 hours the mixture was cooled to room temperature and the viscous melt was dissolved in water and filtered. The molecular weight Mw of the polymer, determined by GPC in accordance with Example 1, was 20 600 g/mol, the polydispersity 4.9.

Example 8

Condensation Product of L-Lysine*HCl, Reaction at 150° C. with NaOH, with Reduced Pressure L-Lysine*HCl (11 g, 60 mmol) and NaOH (2.4 g, 60 mmol) were triturated in a mortar and the mixture was subsequently heated under reduced pressure in a Schlenk tube at 150° C. During the reaction, samples were taken after 14, 24, 38, and 48 hours, dissolved in water, the solution was filtered, and the molecular weights were determined by GPC as described in Example 1 (see Table 8).

TABLE 8

Polycondensation of L-lysine*HCl at 150° C. with NaOH added and with reduced pressure

| Reaction time | Molecular weight (Mw) | Polydispersity |
| --- | --- | --- |
| 14 hours | 5800 g/mol | 3.3 |
| 24 hours | 29 300 g/mol | 8.4 |
| 38 hours | 122 800 g/mol | 24.7 |
| 48 hours | 503 600 g/mol | 133.1 |

Example 9

Condensation Product of L-Lysine*HCl, Reaction at 150° C. with NaOH and Dibutyltin Dilaurate with Reduced Pressure A 4-l four-necked flask equipped with stirrer, internal thermometer, gas inlet tube, and descending condenser with reduced-pressure connection and receiver was charged with 1000 g of L-lysine hydrochloride, 218 g of solid sodium hydroxide, 100 g of water, and 0.3 g of dibutyltin dilaurate and the mixture was heated with stirring at an internal temperature of 150° C. After a reaction time of 5 hours, water was distilled off under reduced pressure (200 mbar), and after the major amount of water had gone over the temperature was slowly raised to 180° C. and the pressure was reduced to 10 mbar. After 8 hours 240 g of water distillate had been collected.

The highly viscous polymer was discharged hot, poured onto a metal cooling plate and then ground finely in a mortar.

The determination of the glass transition temperature gave a Tg of 36.8° C.

For determination of the molecular weight distribution the solid product was dissolved in water and the solution was filtered and subjected to measurement by GPC in accordance with the method specified in Example 1. The weight-average molecular weight Mw was 15 000 g/mol, the polydispersity 5.0

Comparative Example 10

Condensation of L-Lysine without Catalyst (in Analogy to Harada, Bull. Chem. Soc. Japan 1959, 32, 1007-1008)

L-Lysine was heated at 150° C. in a Schlenk tube. After 48 hours the product was dissolved in water, the solution was filtered, and the molecular weight was determined as described in Example 1. The weight-average molecular weight Mw was 2400 g/mol, the polydispersity 2.2.

Comparative Example 11 in Accordance with Rohlfing et al., Arch. Biochem. Biophys. 130, 441 (1969))

L-Lysine was heated at 192° C. under a nitrogen atmosphere in a Schlenk tube. After 3 hours a molecular weight Mw=7400 (polydispersity=3.9) and after 8 hours Mw=15 900 (polydispersity=10) were found. Thereafter crosslinking set out, and after just 24 hours 70% of the material employed was insoluble in water.

Comparative Example 12 in Accordance with Fox et al. (BioSystems 1976, 8, 40-44, Example p. 40, Top of Right-Hand Column)

L-Lysine*HCl was heated together with orthophosphoric acid (1 ml to 0.64 g of lysine hydrochloride) at 195° C. in a Schlenk tube. After 10 hours the reaction product was dissolved in water, the acid was neutralized with NaOH, and the product was analyzed by GPC: weight-average molecular weight Mw=1100, polydispersity=3.1.

Comparative Example 13 in Accordance with Fox et al. (BioSystems 1976, 8, 40-44)

L-Lysine*HCl was heated together with orthophosphoric acid (1 ml to 3.5 g of lysine hydrochloride) at 195° C. in a Schlenk tube. After 10 hours the reaction product was dissolved in water, the acid was neutralized with NaOH, and the product was analyzed by GPC: weight-average molecular weight Mw=4300, polydispersity=1.07.

Example 14

Hydrophobic Modification of Polylysine

A 1-l four-necked flask equipped with stirrer, internal thermometer, gas inlet tube, and descending condenser with reduced-pressure connection and receiver was charged with 100 g of L-lysine hydrochloride, 21.8 g of solid sodium hydroxide, and 20 g of water and the mixture was heated with stirring at an internal temperature of 160° C. After a reaction time of 5 hours, water was distilled off under reduced pressure (200 mbar). Then 10 g of stearic acid were added, the temperature was raised to 180° C. and the batch was left to react for one hour under a pressure of 80 mbar with continued water separation. The highly viscous polymer was discharged hot, poured onto a metal cooling plate and then ground finely in a mortar.

The determination of the glass transition temperature gave a Tg of 29° C.

For determination of the molecular weight distribution the solid product was dissolved in water and the solution was filtered and subjected to measurement by GPC in accordance with the method specified in Example 1. The weight-average molecular weight Mw was 7400 g/mol, the polydispersity 3.0

Example 15

Hydrophobic Modification of Polylysine

A 1-l four-necked flask equipped with stirrer, internal thermometer, gas inlet tube, and descending condenser with reduced-pressure connection and receiver was charged with 100 g of L-lysine hydrochloride, 21.8 g of solid sodium hydroxide, and 20 g of water and the mixture was heated with stirring at an internal temperature of 160° C. After a reaction time of 5 hours, water was distilled off under reduced pressure (200 mbar). Then 30 g of stearic acid were added, the temperature was raised to 180° C. and the batch was left to react for one hour under a pressure of 80 mbar with continued water separation. The highly viscous polymer was discharged hot, poured onto a metal cooling plate and then ground finely in a mortar.

The determination of the glass transition temperature gave a Tg of 36° C.

For determination of the molecular weight distribution the solid product was dissolved in water and the solution was filtered and subjected to measurement by GPC in accordance with the method specified in Example 1. The weight-average molecular weight Mw was 24100 g/mol, the polydispersity 9.3.

Example 16

Subsequent Modification of Polylysine 7.1 g of stearic acid were added to 1.5 g of solid polylysine as per Example 9 and the mixture was heated at 150° C. in a Schlenk tube. After 6 hours it was cooled to room temperature and dissolved in tetrahydrofuran (THF) and the solution was filtered. Subsequently the polymer was precipitated from acetone and the solid was isolated by filtration and dried at 60° C. under reduced pressure.

$^1$H NMR (400 MHz, CDCl$_3$): 4.45 (mb, 1H, O=C—CH—NH—); 4.02 (m, 1H, O=C—CH—NH—) 3.19 (m, 2H, —CH$_2$—NH); 2.31 (t, 2H, —CH$_2$—CH$_2$—COOH); 1.61 (q, 6H, —CH$_2$—CH$_2$—COOH, CH$_2$—CH$_2$—NH); 1.26 (m, 30H, —CH$_2$—CH$_2$—CH$_2$—); 0.86 (t, 3H, —CH$_2$—CH$_3$).

IR: 3280m, 3076w, 2922s, 2852m, 1637m, 1533m, 1456m, 1377w, 1246w.

Example 17

Subsequent Modification of Polylysine 6.7 g of oleic acid were added to 1.5 g of solid polylysine as per Example 9 and the mixture was heated at 150° C. in a Schlenk tube. After 6 hours it was cooled to room temperature and dissolved in tetrahydrofuran (THF), the solution was filtered, and THF was removed under reduced pressure on a rotary evaporator at 60° C.

$^1$H NMR (400 MHz, CDCl$_3$): 5.33 (m, 2H, —CH=CH—); 4.47 (mb, 1H, O=C—CH—NH—); 3.75 (t, 1H, O=C—CH—NH—); 3.2 (m, 2H, —CH$_2$—NH); 2.32 (t, 2H, —CH$_2$—); 2.01 (d, 4H, —CH$_2$—CH=CH—CH$_2$—); 1.85 (q, 2H, O=C—(NH)CH—CH$_2$—); 1.61 (m, 4H, —CH$_2$—CH$_2$—CH$_2$—, CH$_2$—CH$_2$—NH); 1.28 (m, 24H, CH$_2$—CH$_2$—CH$_2$—, —CH$_2$—CH$_2$—CH$_2$—NH); 0.85 (t, 3H —CH$_2$—CH$_3$).

IR: 3295wb, 2926s, 2852m, 1709m, 1639m, 1548w, 1460w.

Example 18

Subsequent Modification of Polylysine 5.5 g of polyethylene glycol-carboxylic acid (average molecular weight 750 g/mol) were added to 1.5 g of solid polylysine as per Example 9, and the mixture was heated at 150° C. in a Schlenk tube. After 6 hours it was cooled to room temperature and taken up in water, and the solution was filtered and freed from low molecular weight constituents using a dialysis tube (MWCO 1000). Subsequently the water was removed via a freeze-drying operation.

$^1$H NMR (400 MHz, CDCl$_3$): 4.39 (m, 1H, O=C—CH—NH—); 3.92 ((m, 1H, O=C—CH—NH—); 3.7-3.2 (m, —O—CH$_2$—CH$_2$—O—); 1.91-1.04 (m, 6H, —CH$_2$—CH$_2$—CH$_2$—NH, CH$_2$—CH$_2$—NH, O=C—(NH)CH—CH$_2$—).

IR: 3298wb, 2881s, 1657m, 1529w, 1466w, 1342m, 1279w, 1240m, 1103s, 962m, 843m.

Example 19

Subsequent Modification of Polylysine 7.0 g of solid polylysine as per Example 9 were suspended in 50 ml of acetic anhydride and the mixture was boiled under reflux for 6 hours. The solvent was then removed under reduced pressure on a rotary evaporator. The yield was quantitative.

$^1$H NMR (400 MHz, CDCl$_3$): 4.39 (m, 1H, O=C—CH—NH—); 3.92 ((m, 1H, O=C—CH—NH—); 3.25 (m, 2H, —CH$_2$—NH); 2.87 (m, 2H, —CH$_2$—NH); 1.98 (s, 3H(O)C—CH$_3$); 1.96 (s, 3H (O)C—CH$_3$); 1.75 (mb, 1H, —CH—CH$_2$—CH$_2$—); 1.48 (mb, 2H, CH$_2$—CH$_2$—NH); 1.31 (mb, 2H, —CH$_2$—CH$_2$—CH$_2$—).

IR: 2931s, 2761w, 2646w, 2114w, 1635m, 1566m, 1490m, 1350m, 1304m, 1241w, 1149m, 1095m, 1026s, 980m, 895m, 825w, 717m.

Example 20

Subsequent Modification of Polylysine 1.5 g of solid polylysine as per Example 9 were suspended in 10 ml of trifluoroacetic anhydride and the mixture was boiled under reflux for 6 hours. Then the solvent was removed under reduced pressure on a rotary evaporator at 40° C. Subsequently the polymer was dried at room temperature under a high vacuum at <0.1 mbar.

Example 21

Subsequent Modification of Polylysine 1.5 g of solid polylysine as per Example 9 were suspended at 25° C. in 100 ml of dry methylene chloride. After 0.3 ml of triethylamine had been added 6 ml of trimethylsilyl chloride were slowly added dropwise. Following the addition the mixture was stirred for 6 hours. It was then extracted with water, the extracts were collected, and the water was removed under reduced pressure on a rotary evaporator at 90° C. The yield of the modified product was quantitative.

$^1$H NMR (400 MHz, CDCl$_3$): 4.15 (mb, 1H, O=C—CH—NH—); 4.00 (m, 1H, O=C—CH—NH—); 3.88 (mb, 1H, O=C—CH—NH—); 3.16-3.07 (m, 2H, —CH$_2$—NH(CO)); 2.93 (mb, 2H, —CH$_2$—NH); 1.80 (mb, 1H, —CH—CHH'—CH$_2$—); 1.70 (mb, 1H, —CH—CHH'—CH$_2$—); 1.48 (mb, 2H, CH$_2$—CH$_2$—NH); 1.31 (mb, 2H, —CH$_2$—CH$_2$—CH$_2$—); 1.18 (td, J=7.34, 3.4 Hz, 6H, Si—(CH$_3$)).

IR: 3218w, 2929s, 2866w, 1660s, 1556m, 1497w, 1393w, 1252w, 1157w, 671m.

Example 22

Modified Polylysine as Transport Reagent

A solution was prepared of 41.8 mg of Congo red in 1 liter of water (6*10$^{-5}$ mol/l). 5 ml of this dye solution were slowly pipetted into 5 ml of a solution of 50 mg of lysine polymer from Example 16 in 5 ml of chloroform, which was contained within a snap lid glass vessel. Two phases formed, with the dye located in the upper, aqueous phase. The snap lid glass was closed and shaken vigorously. After phase separation, the dye was located in the lower, chloroform phase.

The patent or application file contains at least one drawing executed in color. Copies of this patent or patent application publication with color drawing(s) will be provided by the office upon request and payment of the necessary fee.

The systems are depicted in FIG. 1:

The upper phase is the water phase, the lower phase the organic chloroform phase.

Far left: water with dye—top, chloroform—bottom

2nd system from left: water with dye—top, chloroform—bottom, mixed with stearic acid (10 mg/ml), after shaking and renewed phase separation 2nd system from right: water, dye, chloroform, and stearic acid-modified polylysine (10 mg/ml), after shaking and renewed phase separation Far right: chloroform and stearic acid-modified polylysine (10 mg/ml)

Example 23

Complexing of Polylysine with Sodium Dodecyl Sulfate (SDS)

1 g of highly branched polylysine from Example 9 (8.24 mmol $NH_2$ equivalents) was dissolved in 30 ml of MilliQ water and the pH of the solution was adjusted to 3.5 using 0.1 M HCl. In parallel with this, 2.38 g of sodium dodecyl sulfate (SDS, 8.26 mmol) were dissolved in 100 ml of water and the pH of the solution was likewise adjusted to 3.5 using 0.1 M HCl. The SDS solution was then added slowly, with stirring, to the aqueous solution of the polylysine, the reaction mixture turning cloudy and a precipitate being formed. After the end of the addition the mixture was stirred for a further 15 minutes and the precipitate was then isolated by filtration. The filter residue was dissolved in 50 ml of 1-butanol and the butanolic solution was then added slowly to 500 ml of water with a pH of 3.5. The precipitate formed was again isolated by filtration and washed copiously with 2000 ml of water adjusted to a pH of 3.5. The whitish yellow residue was dried over $P_2O_5$ in a desiccator. The yield was quantitative; the degree of loading of the polylysine, based on $NH_2$ groups, was found to be 95%.

$^1$H NMR (400 MHz, $CD_3OD$, rt): 4.28 (br, 1H, COCH(R)NH), 4.00 (t, 2H, J=6.92 Hz, SDS-C(1)H$_2$), 3.89 (br, 1H, COCH(R)NH), 3.23 (m, 2H, CH$_2$—NH), 2.98 (m, 2H, CH$_2$—NH$_2$), 1.86 (br m, 2H, COCH(CH$_2$)NH), 1.66 (q, 2H, J=6.78 Hz, SDS-C(2)H$_2$), 1.58 (br m, 2H, CH$_2$—CH$_2$—NH), 1.38 (br m, 2H, SDS-C(3)H$_2$), 1.35-1.20 (br m, 18H, CH$_2$—CH$_2$—CH$_2$, SDS-C(4)-SDS-C(11))H$_2$), 0.90 (d, 3H, J=6.76 Hz, SDS-C(12)H$_2$). $^{13}$CNMR (100.6 MHz, $CD_3OD$, rt): 168.4 (COCH(R)NH), 67.36 (SDS-C(1)), 52.59 (COCH(R)NH), 52.37 (COCH(R)NH), 38.45 (CH$_2$—NH), 38.20 (CH$_2$—NH), 31.14 (SDS-C(2)), 30.32 (COCH(CH$_2$)NH), 30.12 (COCH(CH$_2$)NH), 28.88, 28.83, 25.55, 28.52 (7×SDS-C(3)-SDS-C(9)), 29.74 (CH$_2$—CH$_2$—NH), 25.01 (SDS-C(10)), 21.80 (SDS-C(11)), 21.36 (CH$_2$—CH$_2$—CH$_2$), 20.99 (CH$_2$—CH$_2$—CH$_2$), 12.54 (SDS-C(12)).

Example 24

Complexing of Polylysine with Sodium Octyl Sulfate (SOS)

The procedure of Example 23 was repeated but using, instead of SDS, 1.92 g of sodium octyl sulfate (SOS).

The yield of whitish yellow solid was quantitative; the degree of loading, based on $NH_2$ groups, was found to be 90%.

$^1$H NMR (400 MHz, $CD_3OD$, rt): 4.29 (br, 1H, COCH(R)NH), 4.00 (d, 2H, J=5.46 Hz, SOS—C(1)H$_2$), 3.89 (br, 1H, COCH(R)NH), 3.24 (m, 2H, CH$_2$—NH), 2.98 (m, 2H, CH$_2$—NH$_2$), 1.88 (br m, 2H, COCH(CH$_2$)NH), 1.67 (br m, 2H, SOS—C(2)H$_2$), 1.60 (br m, 2H, CH$_2$—CH$_2$—NH), 1.40 (br m, 2H, CH$_2$—CH$_2$—CH$_2$), 1.32 (br m, 10H, SOS—C(3)H$_2$—SOS—(C7)H$_2$), 0.91 (d, 3H, J=4.75 Hz, SOS—C(8)H$_2$).

The invention claimed is:

1. A process for preparing a non-crosslinked hyperbranched polylysine which comprises reacting
   (A) a salt of lysine with at least one acid,
   (B) optionally, at least one amino acid other than lysine,
   (C) optionally, at least one dicarboxylic or polycarboxylic acid or copolymerizable derivatives thereof and
   (D) optionally, at least one diamine or polyamine or copolymerizable derivatives thereof,
   (E) optionally, in at least one solvent
   at a temperature from 120 to 200° C.
   in the presence of at least one catalyst (F) selected from the group consisting of
   (F1) tertiary amines and amidines, and
   (F3) alkoxides, alkanoates, chelates or organometallic compounds of metals from groups IIIA to VIIIA or IB to VB in the Periodic Table of the Elements.

2. The process according to claim 1, wherein the reaction time amounts to one to 72 hours.

3. The process according to claim 1, wherein the salt of lysine is a hydrochloride.

4. The process according to claim 1, wherein the molar ratio of amino groups to carboxyl groups in the reaction mixture amounts to between 3:1 to 1:3.

5. The process according to claim 1, wherein the proportions are as follows:
   (B) up to 100 mol % based on (A),
   (C) 0 to 50 mol % based on (A),
   (D) 0 to 50 mol % based on (A),
   (E) 0-200% by weight with respect to the sum of components (A) to (D), and
   (F1) up to 110 mol % with respect to the acid which forms the salt with lysine, and/or
   (F3) 0.1 to 20 mol % with respect to the sum of components (A) to (D).

6. The process according to claim 1, wherein at least one further component (G) is present which besides amino groups and/or carboxyl groups contains hydroxyl groups, mercapto groups, tertiary amine groups, ether groups, urea groups, sulfonic acid groups, phosphonic acid groups, silane groups, siloxane groups, aryl radicals or short- or long-chain alkyl radicals which, optionally, are also partly fluorinated or perfluorinated.

7. The process according to claim 1, wherein at least one further component (H) is present which contains no amino groups and no carboxyl groups but instead contains functional groups other than amino groups or carboxyl groups.

8. The process according to claim 1, wherein at least one further component (I) is present which comprises acid groups, isocyanate groups, keto groups or aldehyde groups or activated double bonds wherein said groups and said double bonds are without amino or carboxyl groups.

9. The process according to claim 1, wherein the polylysine obtained is further reacted with at least one alkylene oxide (J1).

10. The process according to claim 1, wherein the polylysine obtained is further reacted with polyalkylene oxides (J2) which are terminated with amino groups or acid groups and have a functionality of one, two or more.

11. The process according to claim 1, wherein the polylysine obtained is further reacted with alkylating reagents (K).

12. The process according to claim 1, wherein the polylysine obtained is further reacted with saturated or unsaturated long-chain carboxylic acids (L), amino-reactive derivatives thereof, aliphatic or aromatic isocyanates, trialkylsilyl halides, partly or fully fluorinated alcohols, alkyl halides, carboxylic acids or amines.

* * * * *